US007416889B2

(12) United States Patent
Ciombor et al.

(10) Patent No.: US 7,416,889 B2
(45) Date of Patent: Aug. 26, 2008

(54) METHODS AND COMPOSITIONS FOR REPAIRING CARTILAGE

(75) Inventors: Deborah McK. Ciombor, Greenville, RI (US); Roy K. Aaron, Providence, RI (US)

(73) Assignee: Rhode Island Hospital, Providence, RI (US)

( * ) Notice: Subject to any disclaimer, the term of this patent is extended or adjusted under 35 U.S.C. 154(b) by 97 days.

(21) Appl. No.: 11/414,246

(22) Filed: Apr. 27, 2006

(65) Prior Publication Data

US 2007/0253938 A1 Nov. 1, 2007

(51) Int. Cl.

*A61K 35/32* (2006.01)
*C12N 5/08* (2006.01)
*C12N 5/02* (2006.01)
*C12N 5/00* (2006.01)

(52) U.S. Cl. ...................... 435/371; 435/325; 435/366; 424/93.7

(58) Field of Classification Search ...................... None
See application file for complete search history.

(56) References Cited

U.S. PATENT DOCUMENTS

| | | | | |
|---|---|---|---|---|
| 5,858,355 | A * | 1/1999 | Glorioso et al. | 424/93.21 |
| 6,228,356 | B1 * | 5/2001 | Glorioso et al. | 424/93.2 |
| 6,645,764 | B1 | 11/2003 | Adkisson | 435/375 |
| 6,787,136 | B1 * | 9/2004 | Brenner et al. | 424/145.1 |
| 6,835,377 | B2 | 12/2004 | Goldberg et al. | 424/93.7 |
| 2002/0122790 | A1 | 9/2002 | Hunziker | 424/93.7 |
| 2003/0036801 | A1 * | 2/2003 | Schwartz et al. | 623/23.63 |
| 2006/0188501 | A1 * | 8/2006 | Homma et al. | 424/143.1 |
| 2007/0059372 | A1 * | 3/2007 | Johnson | 424/489 |

FOREIGN PATENT DOCUMENTS

| | | | |
|---|---|---|---|
| WO | WO 99/02654 | | 1/1999 |
| WO | WO 03/007805 | A2 | 1/2003 |
| WO | WO 03/007839 | A2 | 1/2003 |
| WO | WO 2004/046305 | A2 | 6/2004 |
| WO | WO 2004/093932 | A1 | 11/2004 |

OTHER PUBLICATIONS

Schwartz, I.M. and Hills, B.A. Synovial Surfactant: Lamellar Bodies in Type B Synoviocytes and Proteolipid in Synovial Fluid and the Articular Lining. British Journal or Rheumatology. 1996, 35(9), 821-827.*
Wu, Q. et al., Journal of Biological Chemistry, 276:35290-35296 (2001).*
Yang, S.Y., et al. FEBS Letters, 522:156-160 (2002).*
Zhen, X., et al., Journal of Biological Chemistry 276:4879-4885 (2001).*
Aaron et al. *Bioelectromagnetics*, 20(7):453-458 (1999).
Aaron et al. *J. Orthop. Res.*, 20(2):233-240 (2002).
Aaron et al. *Clin. Orthop.*, 419:30-37 (2004).
Bellamy et al. *J. Rheumatol.*, 15(12):1833-1840 (1988).
Bostrom et al. *Clin. Orthop.* 355S: S124-A131 (1998).
Bravenboer et al. *J. Orthop. Res.*, 19(5):945-949 (2001).
Busse et al. *Can. Med. Assoc. J.*, 166(4):437-441 (2002).
Carter et al. *Clin. Orthop.*, 355S:S41-S55 (1998).
Ciombor et al. *Osteoarthr. Cartil.*, 11:455-462 (2003).
Claes et al. *Clin. Orthop.*, 355S:S132-S147 (1998).
de Bari et al. *Arthr. Rheum.*, 44(8):1928-1942 (2001).
Dougados, M. *OsteoArthr. Cartil.*, 12:S55-S60 (2004).
Fitzsimmons et al. *J. Cell. Physiol.*, 150(1):84-89 (1992).
Goldspink, G. *Ann. NY Acad. Sci.*, 1019:294-298 (2004).
Guerkov et al. *Clin. Orthop. Rel. Res.*, 384:265-279 (2001).
Heckman et al. *J. Bone Joint Surg.*, 76:26-34 (1994).
Hering et al. *Eur. J. Appl. Physiol.*, 86(5):406-410 (2002).
Ito et al. *Ultrasound Med. Biol.*, 26(1):161-166 (2000).
Jin et al. *J. Orthop. Res.*, 18:899-908 (2000).
Kokubu et al. *Biochem. Biophys. Res. Commun.*, 256(2):284-287 (1999).
Kristiansen et al. *J. Bone Joint Surg.*, 79(7):961-973 (1997).
Naruse et al. *J. Bone Min. Res.*, 18(2):360-369 (2003).
Neidlinger-Wilke et al. *J. Biomechanics*, 28(12):1411-1418 (1995).
Nelson et al. *J. Am. Acad. Orthop. Surg.*, 11(5):344-354 (2003).
Ontiveros et al. *J. Cell. Biochem.*, 88(3):427-437 (2003).
Peyron, J.G., *J. Rheumatol.*, 20(Suppl. 39):10-15 (1993).
Rubin et al. *J. Cell. Physiol.*, 170(1):81-87 (1997).
Rubin et al. *J. Orthop. Res.*, 17(5):639-645 (1999).
Rubin et al. *Am. J. Physiol. Cell Physiol.*, 278:C1126-C1132 (2000).
Rubin et al. *J. Bone Joint Surg.*, 83A(2):259-270 (2001).
Rubin et al. *J. Bone Miner. Res.*, 17(8):1452-1460 (2002).
Rubin et al. *J. Biol. Chem.*, 278(36):34018-34025 (2003).
Ryaby et al. *Trans. Orthop. Res. Soc.*, 7:590 (1992).
Ryaby et al. *Bioelectrochem. Bioenerg.*, 35:87-91 (1994).
Sun et al. *J. Biochem. Material Res.*, 57(3):449-456 (2001).
Tepper et al. *FASEB J.*, Jun. 18 Online: 1-16 (2004).
Tzima et al. *EMBO J.*, 20(17):4639-4647 (2001).
Warden et al. *Ultrasound Med. Biol.*, 27(7):989-998 (2001).
Warden, S.J. *Sports Med.*, 33(2):95-107 (2003).

(Continued)

*Primary Examiner*—Sandra Saucier
*Assistant Examiner*—Aaron J Kosar
(74) *Attorney, Agent, or Firm*—Mintz, Levin, Cohn, Ferris, Glovsky and Popeo, P.C.; Ingrid A. Beattie

(57) ABSTRACT

Disclosed is a method for inducing repair of a joint tissue in a mammal includes the steps of removing a sample of synovial membrane from a joint of the mammal, isolating type B synoviocytes from the membrane to yield a suspension of enriched type B synoviocytes, and introducing the suspension into an injured joint of the mammal as well as medical devices containing enriched synoviocytes and kits for producing such enriched cell populations.

12 Claims, 9 Drawing Sheets

OTHER PUBLICATIONS

Weiss et al. *J. Bone Miner. Res.*, 17(7):1280-1289 (2002).

Chomarat et al., "Contribution of IL-1, CD14, AND CD13 in the increased IL-6 production induced by in vitro monocyte-synoviocyte interactions", *J. Immunol.*, 155:3645-3652 91995).

Mor et al., "The fibroblast-like synovial cell in rheumatoid arthritis: a key player in inflammation and joint destruction", *Clin. Immunol.* 115:118-128 (2005).

Zimmermann et al., "Isolation and characterization of rheumatoid arthritis synovial fibroblasts from primary culture - primary culture cells markedly differ from fourth-passage cells", *Arthritis Res.*, 3:72-76 (2001).

* cited by examiner

SEQUENCE LISTING

```
<160> NUMBER OF SEQ ID NOS: 12

<210> SEQ ID NO 1
<211> LENGTH: 17
<212> TYPE: DNA
<213> ORGANISM: Porcine

<400> SEQUENCE: 1

tgcaggtgac catggcc                                                17


<210> SEQ ID NO 2
<211> LENGTH: 17
<212> TYPE: DNA
<213> ORGANISM: Porcine

<400> SEQUENCE: 2

tgcaggtgac catggcc                                                17
```

-continued

```
<210> SEQ ID NO 3
<211> LENGTH: 21
<212> TYPE: DNA
<213> ORGANISM: Porcine

<400> SEQUENCE: 3

ctgcactcgg ccctggtcaa g                                           21


<210> SEQ ID NO 4
<211> LENGTH: 22
<212> TYPE: DNA
<213> ORGANISM: Porcine

<400> SEQUENCE: 4

gcccaaagac agccatgaca aa                                          22


<210> SEQ ID NO 5
<211> LENGTH: 20
<212> TYPE: DNA
<213> ORGANISM: Porcine

<400> SEQUENCE: 5

cctccggctc ctgctcctct                                             20


<210> SEQ ID NO 6
<211> LENGTH: 19
<212> TYPE: DNA
<213> ORGANISM: Porcine

<400> SEQUENCE: 6

cgtggtttcc tggtcggtg                                              19


<210> SEQ ID NO 7
<211> LENGTH: 19
<212> TYPE: DNA
<213> ORGANISM: Porcine

<400> SEQUENCE: 7

ccatctggct tccagggac                                              19


<210> SEQ ID NO 8
<211> LENGTH: 17
<212> TYPE: DNA
<213> ORGANISM: Porcine

<400> SEQUENCE: 8

ccacgaggcc aggagct                                                17


<210> SEQ ID NO 9
<211> LENGTH: 20
<212> TYPE: DNA
<213> ORGANISM: Porcine

<400> SEQUENCE: 9

cggctaccac atccaaggaa                                             20


<210> SEQ ID NO 10
<211> LENGTH: 18
<212> TYPE: DNA
<213> ORGANISM: Porcine

<400> SEQUENCE: 10
```

-continued

```
gctggaatta ccgcggct                                                    18


<210> SEQ ID NO 11
<211> LENGTH: 24
<212> TYPE: DNA
<213> ORGANISM: Porcine

<400> SEQUENCE: 11

ggaaggagaa gagagcagga tttc                                             24


<210> SEQ ID NO 12
<211> LENGTH: 22
<212> TYPE: DNA
<213> ORGANISM: Porcine

<400> SEQUENCE: 12

ccatctctgg tctcaaccgt ct                                               22
```

METHODS AND COMPOSITIONS FOR REPAIRING CARTILAGE

FIELD OF THE INVENTION

The invention relates to orthopedic injury and repair thereof.

BACKGROUND OF THE INVENTION

Cartilage is a complex, living tissue that lines the bony surface of joints. It provides shock absorption, enabling the joints to withstand weight bearing through the range of motion needed to perform daily activities as well as athletic endeavors. Articular cartilage damage is the most common type of cartilage damage, and can occur as a result either of injury, degeneration caused by wear and tear, or disease. Individuals with cartilage damage often experience stiffness, decreased range of motion, joint pain and/or swelling in the affected area. The pain may prevent involvement in normal activities. Existing medical treatments may help relieve the symptoms of cartilage damage, but they often do not address the cause of the problem. The demand for therapeutic interventions for the treatment of musculoskeletal damage, especially repair or replacement of damaged cartilage, has increased dramatically in recent years.

SUMMARY OF THE INVENTION

The invention provides a solution to a serious and persistent problem in orthopedic medicine. The methods are based upon the discovery that synoviocytes enriched for type B synoviocytes are more effective for cartilage repair compared to a mixed population of cells obtained from synovial membrane tissues. The invention is based on a procedure of quickly processing patient-derived tissue ex vivo during an orthopedic procedure to yield a substantially enriched population of autologous type B synoviocytes suitable for implantation/injection into the recipient.

Accordingly, a method for inducing repair of a joint tissue in a mammal includes the steps of removing a sample of synovial membrane from a joint of the mammal, isolating type B synoviocytes from the membrane to yield a suspension enriched with type B synoviocytes, and introducing the suspension into a site of injury such as an injured joint of the mammal. A purified or enriched type B synoviocyte (or precursor) composition is obtained by separating type B synoviocytes from other cells (e.g., type A synoviocytes) that are present in a tissue explant from the patient. The purified composition is enriched for type B synoviocytes by at least 2-fold, 3-fold, 5-fold, 6-fold, 8-fold or more compared to the the fraction present in an unprocessed cell suspension from explanted tissue. In preferred embodiments, type B synoviocytes comprises at least 85, 90, 95, 98, 99, 100% of the cells in a purified patient-derived cell suspension.

Subjects to be treated with type B synoviocytes include humans suffering from a condition or injury characterized by a cartilage defect or degradation, e.g., osteoarthritis or a traumatic injury to a joint as well as those subject to surgical reconstruction for ears and noses, restoration of a spinal disc, growth plate injuries, and reconstruction of injured tracheal rings. The methods are suitable for veterinary use (e.g., for treatment of dogs, cats, and horses) as well as human clinical treatment.

Enrichment of type B synoviocytes or precursors thereof is carried out by positive selection using reagents that bind to biomarkers for the target cell type or by negative selection. Cell surface markers/biomarkers of type B synoviocyte and precursors thereof include positive markers such as CD9, CD10, CD13, CD29, CD34, CD44, CD49, CD54, CD55, CD59, CD90, CD105, CD106, CD146, CD166, HLA-A, B, or C; negative markers include CD11b, CD14, CD18, CD31, CD45, CD50, CD62e, Strol, HLA-DR.

An exemplary method includes a step in which type A synoviocytes are removed from the mixed population of synoviocytes. For example, type A synoviocytes are removed by negative selection of cells expressing a macrophage/monocyte cell surface antigen such as separation of magnetic polymeric beads coated with an ligand that binds to a macrophage/monocyte specific antigen on the surface of type A synoviocytes. Preferably, the ligand is an antibody or antigen-binding fragment thereof and the macrophage/monocyte cell surface antigen is CD14 or another macrophage/monocyte marker such as CD16 or CD68. Other useful surface antigens to target include CD69, ENG, FCER2, IL2RA for activated macrophages and monocyte/macrophage cell surface markers such as ADAM8, C5R1, CD14, CD163, CD33, CD40, CD63, CD68, CD74, CD86, CHIT1, CHST10, CSF1R, DPP4, FABP4, FCGR1A, HLA-DRA, ICAM2, IL1R2, ITGA1, ITGA2, S100A8, TNFRSF8, TNFSF7. Dendritic cell surface markers include CD1A, CD209, CD40, CD83, CD86, CR2, FCER2, FSCN1.

Unlike earlier methods, the method described herein does not comprise in vitro cell culture to expand the number of cells. A significant advantage of this method is that the timing of the cell fractionation procedure is compatible with that of an orthopedic surgical procedure. For example, synoviocytes are maintained ex vivo for less than 120 minutes. In preferred embodiments, the synoviocytes are maintained ex vivo for less than 90 minutes, e.g., 60, minutes, 45 minutes, or 30 minutes. Another advantage of the procedure is that only one surgical procedure is required. In contrast, earlier methods which include a cell culture step for cell proliferation/differentiation required at least two invasive surgical procedures, one to remove cells and a second one days or weeks later to administer an expanded cell population.

Prior to being returned to the individual from which the cells were obtained, the suspension of enriched type B synoviocytes are contacted with a growth factor. The contacting step is 10, 20 30, 45 minutes; 1,2, 5, 12, 18 hours; 1, 2, 5. 7 days or up to weeks prior to surgery. Preferably, the contacting step is between 1 and 120 minutes, e.g., 30, 60, 90 minutes prior to reintroduction of the cells into a site of injury. For example, prior to introduction into said injured joint, the cells are contacted with growth factor is selected from the group consisting of TGFβ1, BMP-2, BMP-4, and BMP-7. Other factors are selected from the group consisting of GDF5, TGFβ3, IGF1, FGF, PDGF, Osteogenin, and Platlet Rich Plasma (PRP). For example, the cells are cultured in media containing 2-500 ng/ml GDF-5, 10-500 ng/ml IGF-1, 1-100 ng/ml PDGF, 0.1-100 ng/ml osteogenin and/or 1-100 ng/ml TGFβ3. Optionally, the suspension of enriched type B synoviocytes are subjected to a physical force, eg. An electromagnetic field, prior to introduction into the injured joint. Or the In some cases, the cells the cells are formulated in an adhesive matrix such as a glue or cement prior to reintroduction. Optionally, the method also includes the administration a growth factor such as TGFβ1 into the joint during or after administration of the cells.

Also within the invention is a biocompatible device for implantation into a mammalian subject. The device contains a solid support scaffold and a population of autologous synoviocytes, the synoviocytes being obtained from a synovial membrane of the subject and being enriched for type B synoviocytes. For example, the scaffold is selected from the group consisting of a mesh, screw, bolt, and pin. For large bone grafts or repair of tendons, e.g., Achilles tendon, the cells are seeded onto a grid structure such as a titanium mesh prior to reintroduction into the patient. For tendon repair, the cell-seeded mesh is used as an anchor of the tendon into the bone thereby repairing a junction that was ruptured by an injury. The support or scaffold is permanent or biodegradable. For example, devices are formed of biocompatible polyhydroxyalkanoates and degrade over a period of a year under physiological conditions. Exemplary devices to be seeded with enriched type B synoviocytes include sutures, suture fasteners, meniscus repair devices, rivets, tacks, staples, screws (including interference screws), bone plates and bone plating systems, surgical mesh, repair patches, slings, orthopedic pins (including bone filling augmentation material), adhesion barriers, articular cartilage repair devices, tendon repair devices, bulking and filling agents, meniscus regeneration devices, ligament and tendon grafts, spinal fusion cages, bone graft substitutes, and bone dowels.

A kit for use in orthopedic surgery contains the following assembly of items packaged together: a tissue-disrupting enzyme, a tissue digestion chamber, a dispersed cell chamber, a macrophage/monocyte specific ligand linked to a magnetic particle, and a magnet. Instructions for use of the items in the cell enrichment procedure. The enzyme is any enzyme suitable for disrupting cells from tissue such as trypsin or collagenase, and the macrophage/monocyte specific ligand is any ligand such as an antibody that binds to a cell surface protein of the surface of a macrophage or monocyte. For example, the ligand is a CD14 specific antibody or CD14-binding fragment thereof linked to a particle such as a magnetic bead.

Enriched cells are administered as a cell suspension in a pharmaceutically acceptable medium for reintroduction into the patient. For example, reintroduction of cells is carried out by injection or implantation of a support scaffold or gel containing the cells. Injection is local, i.e. directly into a damaged or compromised joint or insertion point of a tendon into a bone. The technique optimizes chondrogenic activity of synoviocytes and shortens the time required for cartilage repair once the cells have been administered.

Polypeptides or other compounds described herein are to be "substantially pure" when they are within preparations that are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, polyacrylaminde gel electrophoresis, or HPLC analysis. The polypeptide is purified from MSC culture media or recombinantly produced.

By repairing or regenerating an injured or damaged joint is meant restoring mobility of the joint and/or reducing pain associated with movement of the joint. Joint mobility function and pain assessment are measured by methods known in the art. The cells are administered to the subject to reduce the severity of chronic joint disease as well as to speed the healing of surgical repairs to acute injuries. The cell therapy methods are carried out alone in conjunction with a surgical procedure or as an adjunct therapy to other methods such as a minced cartilage, autologous chondrocyte transplantion (e.g., Genzyme Carticel), microfracture, osteochondral transplant or articular paste. The methods improve the outcome of these methods.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

DETAILED DESCRIPTION

Figure 1:
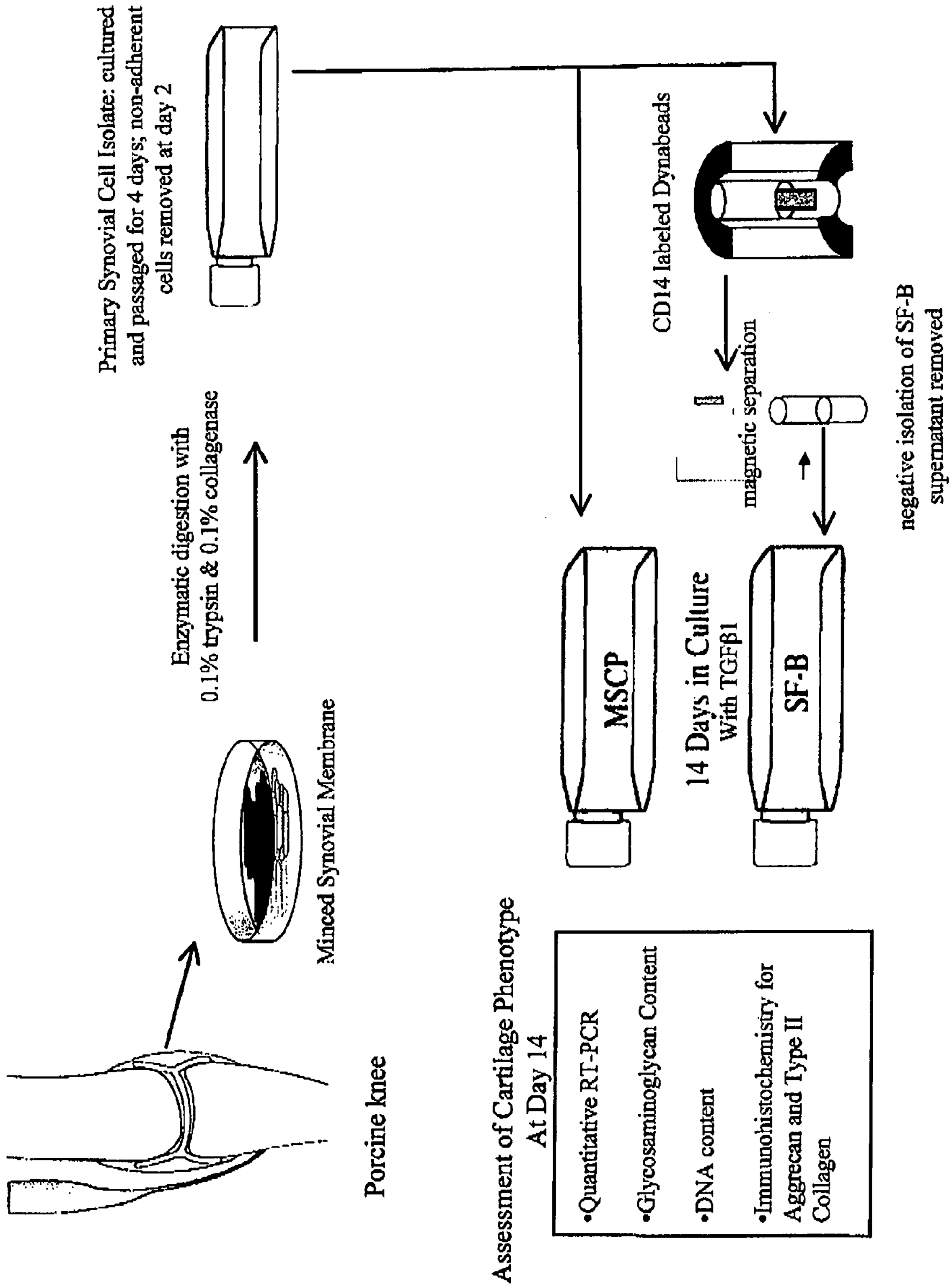
FIG. 1 is is a diagrammatic representation of the protocol for isolation and purification of SF-B synovial cells for use in a tissue-engineered construct.

Currently available cartilage repair techniques have limitations, including limited healing, high cost, breakdown of the tissue implant leading to loss of function, and limited availability of competent cellular components. Techniques dependent on ingrowth from the surrounding articular cartilage as a supplier of functionally active cells have to date proven unsuccessful. A competent cell source is a critical element of a successful tissue-engineered cartilage construct. In seeking a solution to this problem, several laboratories have investigated such multipotential cells as periosteal, perichondrial, bone marrow, adipocyte and synovial cells, all of which possess osteogenic and chondrogenic potential. This capacity to replicate and differentiate makes these cells candidates for use in cartilage repair.

Synovial cells display significant chondrogenic potential in vivo. Synovium has a propensity for forming cartilage, as seen in the pathologic condition synovial chondromatosis. Synovially derived cells share several properties with chondrocytes, including the ability to produce cartilage oligomeric matrix proteins, link proteins, and sulfated glycosaminoglycans. Chondrocytes and synovial cells in fact derive from a common progenitor and exist in a close functional relationship throughout adult life as well as ontogenetically.

Synovium is a surgically relevant tissue that is available to surgeons intraoperatively. The tissue is reasonably abundant, and simple to excise, making it a convenient source of autologous cells for a tissue-engineered product. The synovial membrane, a cellular lining adjacent to the joint capsule and intra-articular bone, comprises two cell populations loosely set in a specialized extracellular matrix: macrophage-like (type A) synoviocytes and locally derived fibroblast-like (type B) synoviocytes.

Existing technologies for isolating these cells are tedious and time-consuming, and require an extraoperative culture component. In contrast, the methods described herein overcome many of the drawbacks of earlier techniques thereby rendering themselves to autologous cell therapy. Negative isolation is used to highly enrich for a population of synovially derived type B fibroblasts (SF-B). The cells are purified using an antibody directed to a monocyte/macrophage membrane antigen, which separates them from the type A synoviocytes. A cell population that is enriched for Type B synoviocytes exhibit significantly enhanced chondrogenic potential compared to the primary isolate. In this paper, we examine and characterize the chondrogenic potential of SF-B under the influence of TGF$\beta_1$, and we describe the in vitro proliferation and differentiation responses of purified SF-B to TGF$\beta_1$ in comparison to a control group of unpurified mixed synovial cell population (MSCP).

Joint, Cartilage, and Tissue Disorders

Injuries or disorders to be treated include injury to an articular surface of a joint, both partial and full-thickness lesions, injury to a meniscus, injury to a growth plate, injury to another cartilage structure such as ear, nose, tracheal ring, use in other reconstructive procedures where the placement of cartilage may provide symptomatic relief such as for urinary incontinence, osteoarhritis as well as tendon, ligament or meniscal repair. For example, the cells are useful to provide a cell source to reanchor a torn tendon or ligament with a scaffold. A scaffold using the cells described herein promote regrowth of the attachment similar to the original naturally-occurring anchor.

Veterinary Applications

Canine osteoarthritis is a prevalent clinical disorder that is treated using the methods described herein. Osteoarthritis afflicts an estimated one in five adult dogs; an estimated 8 million dogs suffer from this degenerative, potentially debilitating disease. Yet, many owners do not recognize the signs of chronic canine pain. While any dog can develop osteoarthritis, those most at risk are large breeds, geriatric dogs, very active dogs (such as working or sporting animals), and those with inherited joint abnormalities such as hip or elbow dysplasia.

Equine degenerative joint disease such as osteoarthritis is a cause of lameness and impaired performance in horses. As with humans and other mammals, degenerative joint diseases which affect horses are progressive disorders of synovial joints characterized by articular cartilage degeneration and joint effusion. Acute or chronic trauma, overuse, developmental disease, joint instability and old age leads to synovitis, impaired chondrocyte metabolism, and the formation of fissures in the joint cartilage.

Enriched Type B Synoviocyte Cell Compositions

Isolation of an autologous, relevant cell source is the first step necessary to initiate cartilage repair. Precursor cell are isolated from an individual's own synovial tissue and used to create a biocomposite which, when placed into the cartilage lesion, recreates functional hyaline cartilage. The methos is preferably carried out as follows:

Step 1. Approximately 1 gram of synovial tissue is removed from the patient at surgery. The tissue is removed from either the joint to be repaired or the contra-lateral joint, e.g,, a right or left knee or elbow.

Step 2. The patient's own cartilage precursor cells are isolated in the operating room by enzymatic digestion and magnetic bead negative isolation with an antibody to CD14 using a commercially available reagents.

Step 3. The selected cells are replaced into the surgically prepared repair site along with a treatment regimen consisting of an experimentally determined growth factor sequence. The treatment regimen consists of a proliferation factor (eg, FGF 2, PDGF$\beta$), a progression/differentiation factor (eg TGF$\beta$1), and a maturation factor (IGF1, insulin or a BMP). As an example, FGF 2 (0.1-50 ng); TGF1$\beta$1 (1.0-40 ng) and IGF 1 (1-500 ng) is included with the cellular component to initiate repair.

Step 4. The defect is closed with a patch of periosteum harvested from the proximal medial tibia.

Step 5. The patient's knee is closed in standard fashion, sutured and the skin is dressed.

Therapeutic Administration

The invention includes administering to a subject a composition comprising an enriched population of Type B synoviocytes to articular joints or other tissues in which cartilage has been damaged, compromised or diseased.

For human therapy, an effective amount of a therapeutic compound is preferably from about 0.5 Million to 25 million cells. Preferably, the cells are administered at a dose of 0.5 to 1.5 Million cells in a liquid volume or seeded onto/into a scaffold, patch, or gel support. For example, cells in solution are administered in a volume of 100-500 microliters, e.g., 50, 100, 150, 200, 250, 400 microliters. In one example, 300,000 cells/100 μl are delivered. Effective doses vary, as recognized by those skilled in the art, depending on route of administration, excipient usage, and coadministration with other therapeutic treatments including use of other agents or therapeutic agents for treating, preventing or alleviating a symptom of a joint disease or injury.

The pharmaceutical compound is administered to such an individual using methods known in the art. Preferably, the compound is administered locally, e.g., directly into an articular joint. The cells are optionally formulated as a component of a cocktail of cytokines and/or growth factors such as those described above. Examples of formulations suitable for parenteral administration include aqueous solutions of the active agent in an isotonic saline solution or another standard pharmaceutically acceptable excipient.

The cell-based compositions are effective upon direct contact of the compound with the affected tissue. Additionally, compositions are administered by implanting (e.g. directly into a joint) optionally a solid or resorbable matrix which slowly releases the compounds and cells into adjacent and surrounding tissues of the subject is adminstered. Alternatively, the cells and/or matrix is coated or impregnated on a medical device that is placed in a joint, bone, or cartilagruous tissue.

Therapeutic compositions are administered in a pharmaceutically acceptable carrier (e.g., physiological saline). Carriers are selected on the basis of mode and route of administration and standard pharmaceutical practice. A therapeutically effective amount of a therapeutic composition (e.g., cells, growth factors, differentiation factors) is an amount which is capable of producing a medically desirable result, e.g., increased mobility or reduced pain associated with joint movement, in a treated animal. A medically desirable result is a reduction in pain (measured, e.g., using a visual analog pain scale described in Peyron et al., 1993, J. Rheumatol. 20 (suppl.39):10-15) or increased ability to move the joint (measured, e.g., using an art-recognized standard disease specific scoring system, WOMAC, or the joint specific scoring system, KOOS, (Bellamy, et al. J Rheumatology, 1988; 15:1833-40 and Dougados, M, Ostroarthritis and Cartilage, 2004; 12 Suppl A:S55-60 ).

As is well known in the medical arts, dosage for any one animal depends on many factors, including the animal's size, body surface area, age, the particular compound to be administered, sex, time and route of administration, general health, and other drugs being administered concurrently. Administration is generally local to an injured or inflamed joint, e.g., the cell suspension is delivered to the synovial cavity. For example, cells are injected into a knee joint using a fine (e.g., 14-22 gauge, preferably 18-22 gauge) needle.

The following reagents and methods were used to generate the data described herein.

Harvest and Digestion of Synovial Tissue

Tissue was aseptically harvested from the knee joints of anesthetized porcine adults. The tissue was finely minced and placed in a digestion medium containing 0.1% trypsin and 0.1% collagenase P (Roche Applied Science, Indianapolis, Ind.) in Dulbecco's Modified Eagle's Medium (DMEM)/10% fetal bovine serum (FBS) for 2 hours at 37° C. The cell suspension was passed through a 70-μm nylon filter (Falcon), and the filtrate was centrifuged. The recovered cells were maintained in primary culture for 4 days (DMEM/10% FBS, 100 U/mL penicillin, 100 μg/mL streptomycin, in T150 flasks (Falcon). The non-adherent cells were removed at Days 2 and 4 of culture, and the remaining cells were subjected to purification as described below.

Synovial Type B Fibroblast (SF-B) Purification

Dynabeads M-450 CD14 are uniform, superparamagnetic polystyrene beads coated with a primary monoclonal antibody specific for the CD14 membrane antigen. Adherent cells were released by short-term trypsinization for less than 2 minutes (0.25% trypsin/0.2% EDTA, GIBCO/Invitrogen, Carlsbad, Calif.). The cells ($10^7$/ mL) were then incubated in 4 mL PBS, 2% FBS, and Dynabeads M-450 CD14 (clone RMO52; Dynal/Invitrogen), at pH 7.2 to 7.6 for 1 hour at 4° C. with gentle tilting and rotation. Additional PBS/2% FBS was then added to reach a final volume of 10 mL. The Dynal Magnetic Particle Concentrator®-MPC1 (Dynal/Invitrogen, Oslo, Norway) was used to separate Dynabeads from heterogeneous liquid samples. The cells (monocytes and macrophages) bound to the conjugated CD14, and the free unbound Dynabeads were collected by magnetic separation using the Dynal MPC-1. The remaining supernatant containing the purified SF-B was then plated.

Cell Culture

Following washing and counting, samples of $0.5\times10^6$ cells were centrifuged at 1200 rpm for 5 minutes to form a pellet. The pellets were cultured at 37° C., in 5% $CO_2$, in defined differentiation medium consisting of high-glucose DMEM, 40 μg/mL proline, 100 nM dexamethasone, 0.1 mM ascorbic acid 2-phosphate (Wako Chemicals USA, Inc., Richmond, Va.), 100 U/ml penicillin, 100 mg/L streptomycin, and ITS+ Premix (Collaborative Biomedical Products, Bedford, Mass.), and bovine serum albumin (1.25 μg/mL), with varying concentrations of recombinant human TGF$\beta_1$, 0 to 40 ng/mL (R & D Systems Inc., Minneapolis, Minn.). After 3 days, the pellets were transferred to 24-well plates on an orbital shaker for another 18 days in identical medium. The time points for assessment were Days 3, 7, 14, and 21.

A schematic representation of the isolation, digestion, and purification protocol is shown in FIG. 1. Three experimental protocols were established: (1) synovial tissue, primary cell isolate (SCI), MSCP, and purified SF-B were compared for the quantitative expression of vimentin and CD-14 mRNA; (2) SF-B and MSCP were compared for their proliferation and differentiation capacities under treatment with 0, 2, and 20 ng/mL of TGF$\beta_1$; and (3) the proliferation and differentiation responses of purified SF-B to 0, 2, 10, 20, and 40 ng/mL of TGF$\beta_1$ were characterized. Multiple experiments were performed for each protocol.

Histology and Immunohistochemistry

Pellets were fixed for 24 hours at 4° C. in 4% paraformaldehyde in PBS (pH 7.4), embedded in paraffin, and sectioned at 5 μm. Consecutive sections were stained with Safranin O/Fast Green for sulfated glycosaminoglycans (GAG) and were immunostained with an HRP-conjugated monoclonal antibody against porcine collagen type II (NeoMarkers, Fremont, Calif.). Immunohistochemical sections were hydrated, incubated for 30 minutes at room temperature with 2 mg/mL testicular hyaluronidase in PBS (pH 5), rinsed with PBS, incubated for 30 minutes with normal goat serum diluted at 1:10 in PBS and for 1 hour with the primary antibody, stained using a kit (Vectastain ABC, Burlingame, Calif.), and counterstained with hematoxylin.

Biochemical Analyses

Pellets were digested for 15 hours at 60° C. in 100 μL papain in PBE buffer (125 μg/mL enzyme in 100 mM phosphate, 10 mM EDTA, containing 10 mM cysteine, pH 6.5). GAG content was determined by a colorimetric assay with 1,9 dimethylmethylene blue at a wavelength of 525 nm at pH 3.0 with bovine chondroitin sulfate as a standard. DNA was measured by the Hoechst 33258 dye-binding method to double-stranded DNA.

RNA Isolation and Real-Time Quantitative RT-PCR

At each time point, three pellets were pooled for studies of gene expression. Total RNA was extracted from pellets by homogenization using an RNase-free pestle in TRIzol reagent (Life Technologies/Invitrogen, Grand Island, N.Y.) and RNeasy Mini Kit (Qiagen, Valencia, Calif.). mRNA for collagens Type I and II, aggrecan, and cell marker proteins was quantified by real-time quantitative reverse transcriptase (RT)-PCR with DNA Engine Opticon™ system (MJ Research, Inc., Waltham, Mass.). For the genes of interest, porcine-specific PCR primers (Table 1) were designed according to the sequences available in GenBank using Gene-Tool software (BioTools, Inc., Edmonton, Alberta, Canada).

TABLE 1

Sequences of porcine primers for real-time quantitative RT-PCR

| Target Gene | Access. Number | Forward Primer (5' to 3') | Reverse Primer (5' to 3') | Amplicon Size |
|---|---|---|---|---|
| Aggrecan | AF201722 | TGCAGGTGACCATGGCC (SEQ ID NO:1) | TGCAGGTGACCATGGCC (SEQ ID NO:2) | 79 |
| CD-14 | AF132037 | CTGCACTCGGCCCTGGTCAAG (SEQ. ID NO:3) | GCCCAAAGACAGCCATGACAAA (SEQ ID NO:4) | 148 |
| Collagen I (al) | AF201723 | CCTCCGGCTCCTGCTCCTCT (SEQ ID NO:5) | CGTGGTTTCCTGGTCGGTG (SEQ ID NO:6) | 316 |
| Collagen II (al) | AF201724 | CCATCTGGCTTCCAGGGAC (SEQ ID NO:7) | CCACGAGGCCAGGAGCT (SEQ ID NO:8) | 106 |
| 18S | | CGGCTACCACATCCAAGGAA (SEQ ID NO:9) | GCTGGAATTACCGCGGCT (SEQ ID NO:10) | 180 |
| Vimentin | AU058707 | GGAAGGAGAAGAGAGCAGGATTTC (SEQ ID NO:11) | CCATCTCTGGTCTCAACCGTCT (SEQ ID NO:12) | 144 |

RNA from synovium, the primary synovial cell isolate (SCI), MSCP pellets, and SF-B pellets (100-300 ng each) were used for oligo$(dT)_{12-18}$-primed cDNA synthesis by SuperScript™II RT (Invitrogen, Carlsbad, Calif.). The DyNAmo™ SYBR Green qPCR kit (Finnzymes, Espoo, Finland) was employed for quantitative real-time analysis of the cDNA samples from the different groups. The cycle parameters were 95° C. for 10 minutes to activate the Tbr DNA polymerase, 39 cycles at 94° C. for 10 seconds for denaturation, 55° C. for 20 seconds for annealing and 72° C. for 20 seconds for extension. The final extension was performed at 72° C. for 5 minutes. At the same time, 18S RNA was amplified and served as an internal control. The cycle threshold (Ct) values for 18S RNA and that of the samples were measured and calculated by Intuitive Opticon Monitor™ software (MJ Research, Inc., Waltham, Mass.). Relative transcript levels were calculated as $\chi=2^{-\Delta\Delta Ct}$, in which $\Delta\Delta Ct=\Delta E-\Delta C$, and $\Delta E=Ct_{exp}-Ct_{18s}$; $\Delta C=Ct_{ctl}-Ct_{18s}$.

Statistical Analysis

Statistical significance was assessed by one-way analysis of variance (ANOVA); P values less than 0.05 were considered statistically significant. Each experimental group contained no fewer than 3 samples.

Comparison of Cell Population Following Purification

Figure 2:
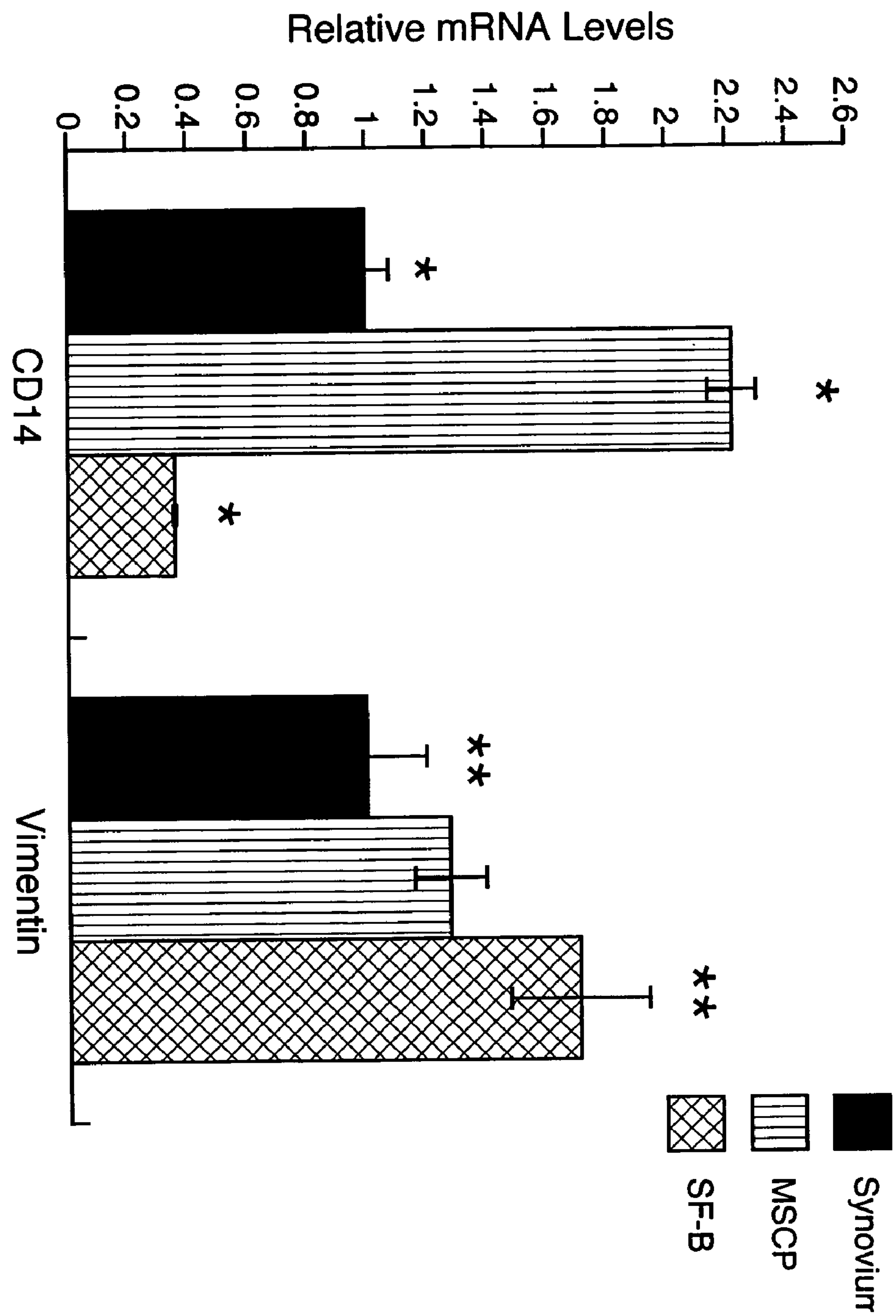
FIG. 2 is a bar graph showing the effect of cell purification by magnetic bead separation upon the relative expression levels of CD14 and vimentin mRNA. Synovium, primary synovial cell isolate (MSCP), and purified SF-B were compared for CD14 (marker for the monocyte /macrophage cell lineage) and vimentin (marker for the mesenchymal cell lineage) mRNA levels by real-time quantitative RT-PCR. The MSCP cells showed a significantly greater amount of CD14 than did either the primary tissue or the purified cells, indicating a higher content of cells of the macrophage lineage in that preparation. The purified SF-B cells show a significant reduction of CD14, indicating the elimination of macrophages following the purification process. The SF-B group expressed the greatest concentration of mRNA for vimentin, further indicating the removal of non-fibroblastic cells from the preparation following the magnetic bead separations. The results were expressed as fold increase above synovial tissue control (*P=0.001; **P=0.05).

Real-time quantitative RT-PCR for CD14, a strongly expressed cell surface marker on monocytes and macrophages, and vimentin, a mesenchymal cell marker, was used to detect the relative mRNA expression levels of macrophage-derived MSCP and SF-B respectively in different tissue and cell samples (FIG. 2). Compared to expression in freshly isolated synovium, CD14 mRNA content increased 122% in the primary synovial cell isolate (SCI), indicating an enrichment of MSCP. CD14 mRNA content decreased by 64% following the negative isolation, indicating the elimination of MSCP from the cell pool. Vimentin mRNA was increased 28% in MSCP over the native tissue following the primary digestion and removal of non-adherent cells. Purification by negative isolation yielded a 71% increase in mRNA for vimentin, indicating an enrichment of the SF-B population.

$TGF\beta_1$-Induced Cartilage Differentiation

Figure 3:
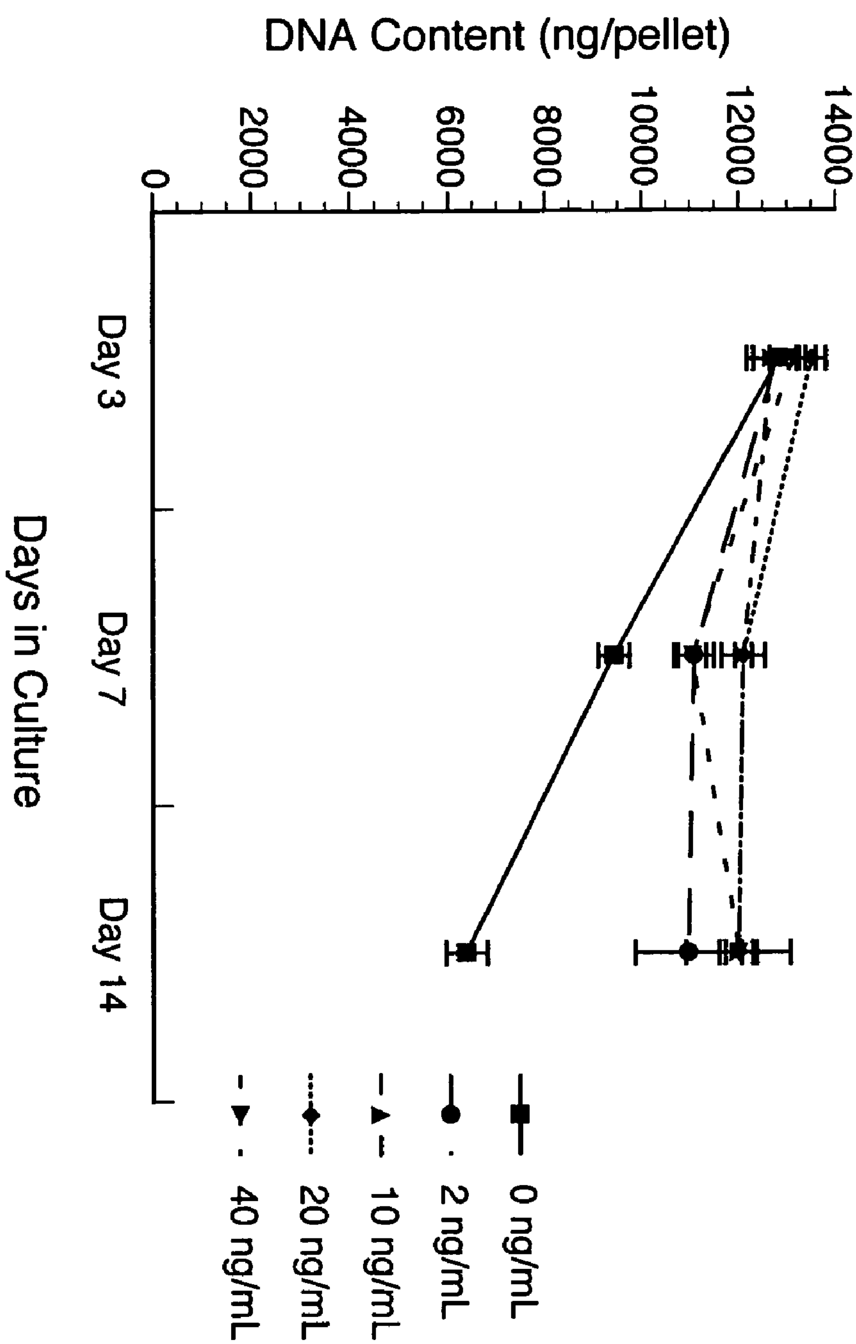
FIG. 3 is line graph showing the response of cells to the presence or absence of $TGF\beta_1$. The DNA content at Days 7 and 14 of culture is shown in response to concentrations of $TGF\beta_1$ varying from 0 ng/mL to 40 ng/mL. Unsupplemented controls showed a significant cell loss by Day 3, whereas supplementation with growth factor attenuates cell loss in all groups. Data for SF-B pellets is shown. Error bars represent the mean±SD for n=3.

Supplementation with $TGF\beta_1$ is used for maintenance of the cultures. Pellets cultured in basal medium without growth factor supplementation demonstrated declining DNA content. Cell number per pellet in the unsupplemented control group dropped by at least 50% by Day 14 (FIG. 3). With $TGF\beta_1$ supplementation, the cell number per pellet decreased to 87% of Day 0 content by Day 7 and was maintained with no significant change through Day 14 with doses of 2 and 10 ng/mL $TGF\beta_1$ respectively. $TGF\beta_1$ supplementation yielded pellets with a stable DNA content per pellet compared to the unsupplemented controls. This effect was maintained over the entire culture period.

Figure 4:
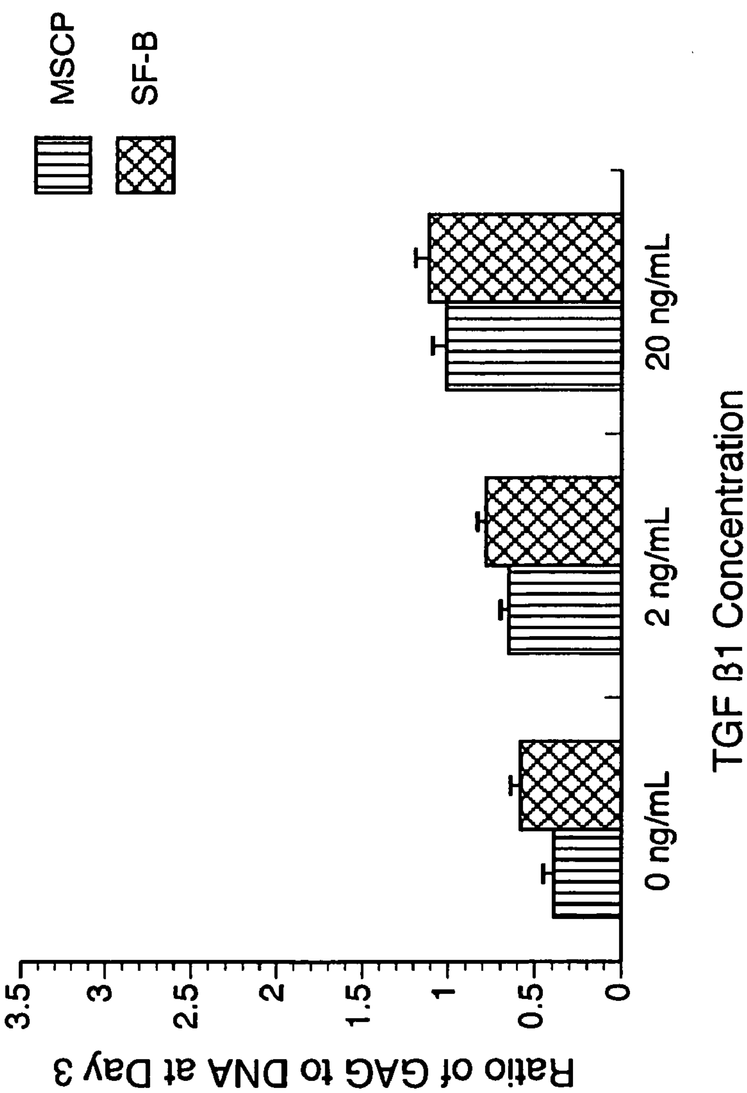
FIG. 4 is a bar graph showing the effect of varied concentrations of $TGF\beta_1$ on MSCP and SF-B pellets at Day 3. The ratio of GAG to DNA, a measure of chondrogenesis, was compared by biochemical analysis. Both cell populations increased GAG production in response to increasing $TGF\beta_1$ concentrations; however, the absolute ratios were always higher in the purified SF-B group. Error bars represent the mean±SD for n=3.
Figure 5:
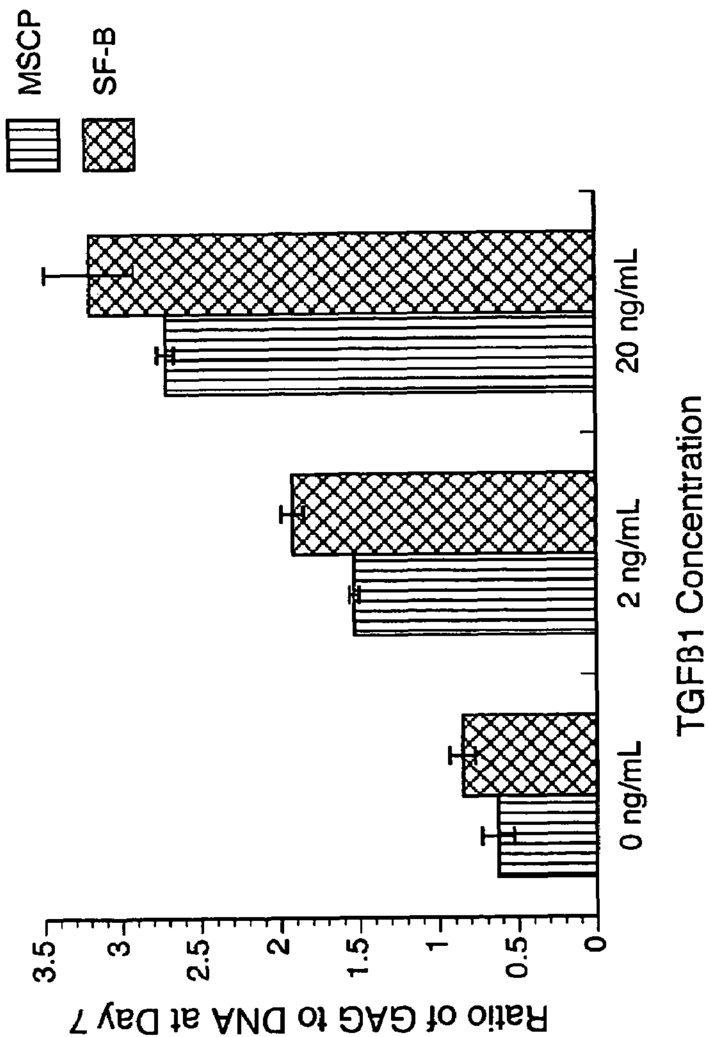
FIG. 5 is a bar graph showing the effect of varied concentrations of $TGF\beta_1$ on MSCP and SF-B pellets at Day 7. The ratio of GAG to DNA, a measure of chondrogenesis, was compared by biochemical analysis. Both cell populations increased GAG production in response to increasing $TGF\beta_1$ concentrations; however, the absolute ratios were always higher in the purified SF-B group. Error bars represent the mean±SD for n=3.
Figure 6:
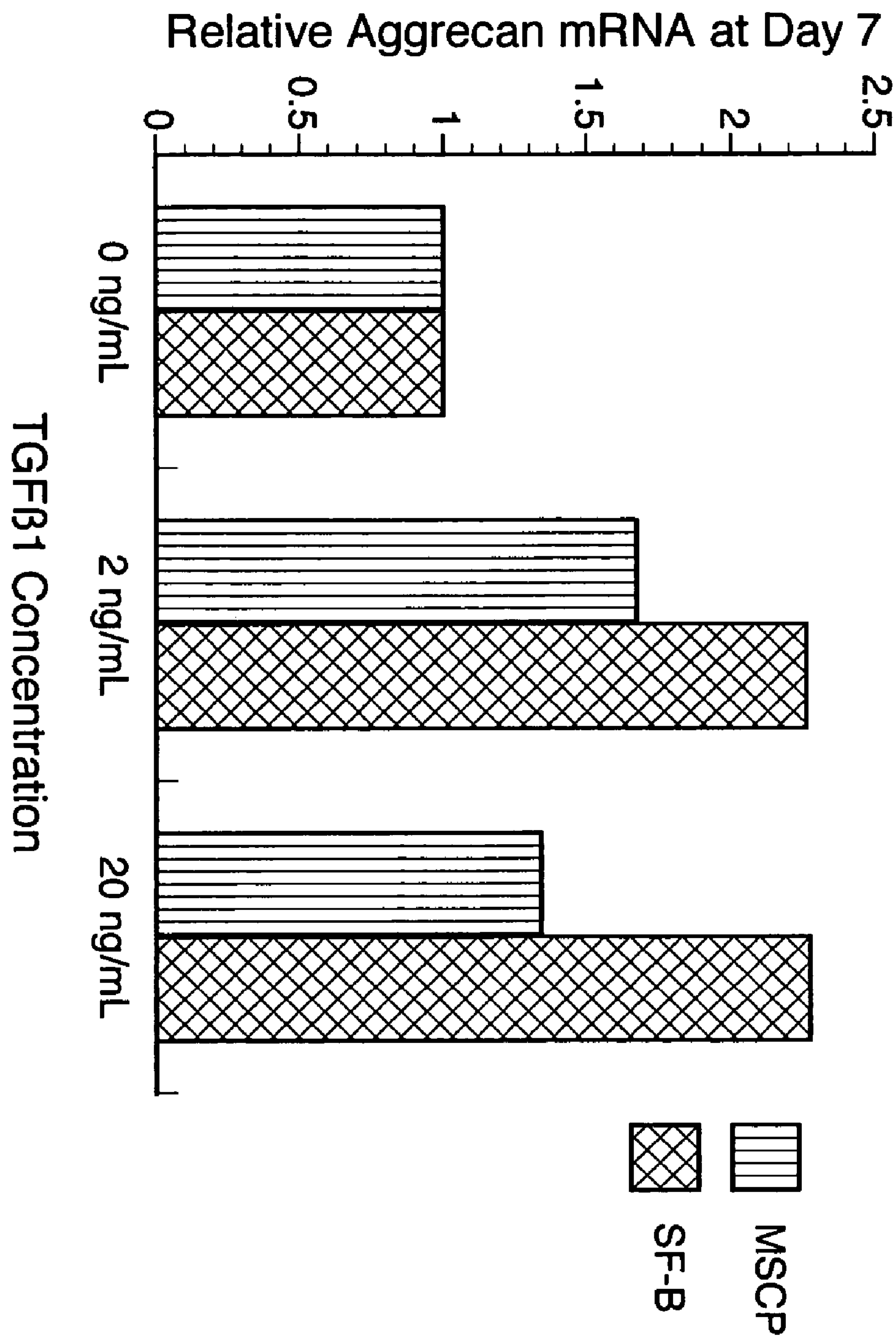
FIG. 6 is a bar graph showing the relative expression levels of aggrecan mRNA at Day 7. The expression of aggrecan mRNA, measured by quantitative real time RT-PCR, indicates that pellets of SF-B cells respond to increasing amounts of $TGF\beta_1$ by increasing the production of messenger RNA for an important extracellular matrix constituent. Three samples were pooled to provide adequate material for each run.

At Day 3, MSCP pellets and SF-B pellets yielded a similar ratio of GAG to DNA (FIG. 4). Due to the small sample size, the observed trend toward a higher GAG/DNA ratio with increasing doses of $TGF\beta_1$ did not reach statistical significance. With supplementation of 20 ng/mL of $TGF\beta_1$, SF-B pellets yielded the highest DNA content per pellet (data not shown). Following 7 days of treatment with $TGF\beta_1$, biochemical analysis showed that, compared to MSCP pellets, SF-B pellets yielded higher amounts of DNA and GAG per pellet. The ratio of GAG to DNA seen in the SF-B pellets was significantly higher in all treatment groups. This result was shown to be dependent on the concentration of $TGF\beta_1$ (FIG. 5). Biochemical analysis at Day 21 showed a similar result. Quantitative RT-PCR showed that SF-B pellets yielded more collagen type II and aggrecan MRNA than did the corresponding MSCP pellets at Day 7, supporting the biochemical findings (FIG. 6).

Differential Effect of $TGF\beta_1$ Concentration on SF-B Pellets

Figure 7:
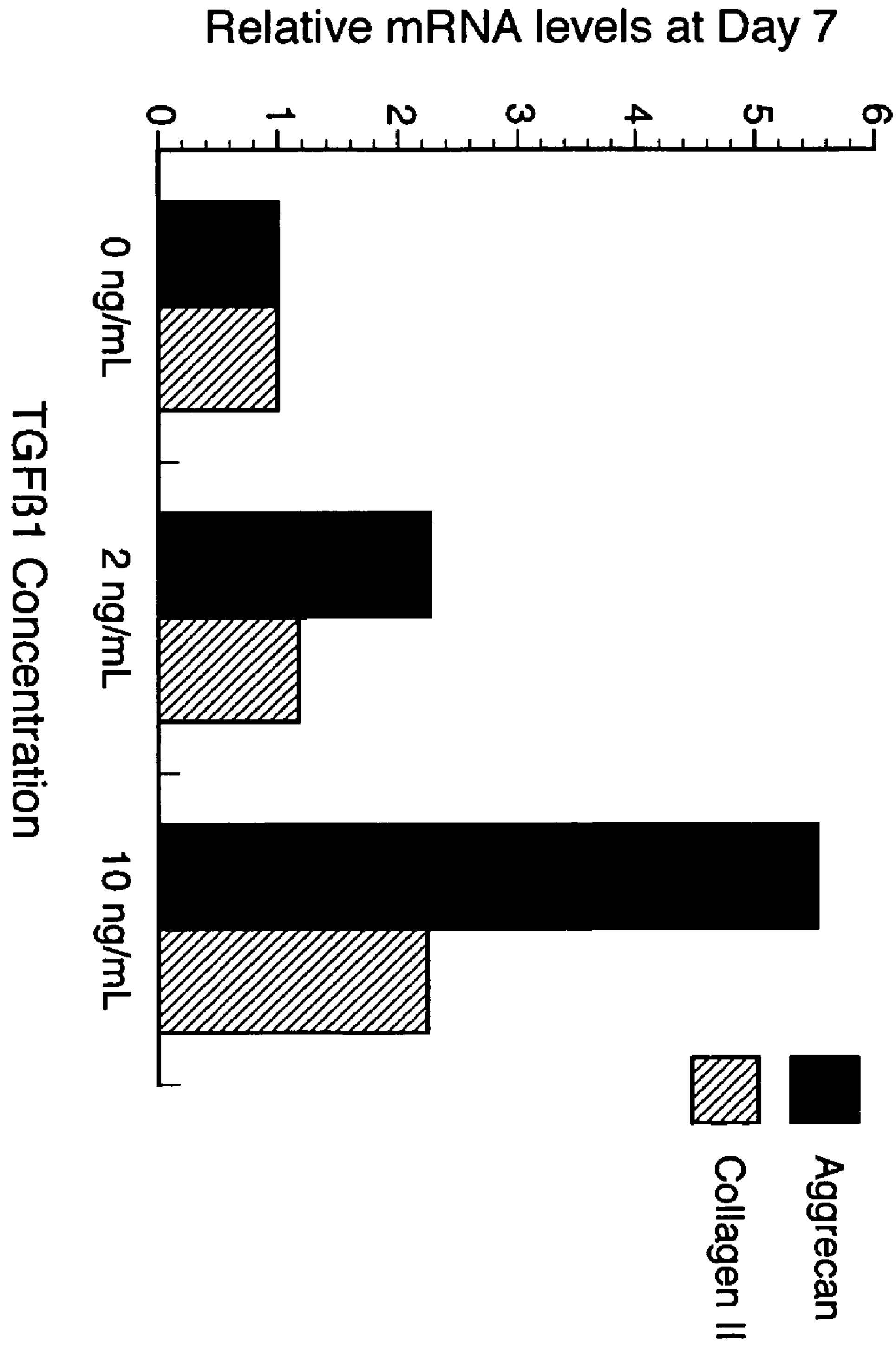
FIG. 7 is a bar graph showing the relative expression levels of collagen type II and aggrecan at Day 7. Quantitative real time RT-PCR assessment shows an increased response from purified SF-B cells in both aggrecan and collagen II mRNA, the two major cartilage extracellular matrix proteins, with increasing doses of TGF$\beta_1$. Three samples were pooled to provide adequate material for each run.
Figure 8:
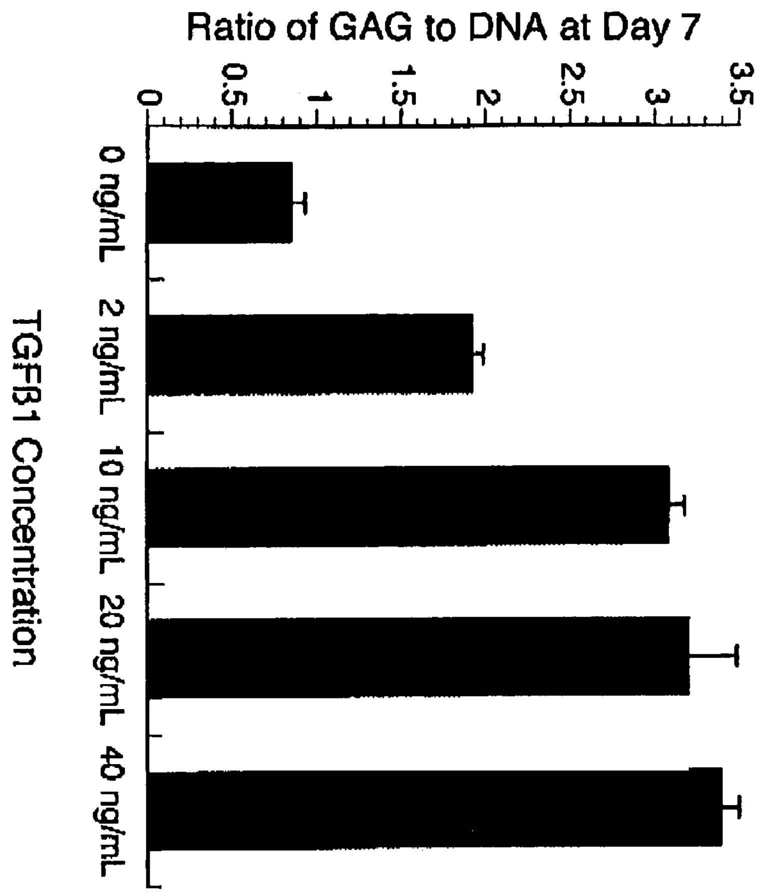
FIG. 8. The response of purified SF-B cells to increasing doses of TGF$\beta_1$ at Day 7. The ratio of GAG to DNA, a measure of chondrogenesis, shows a plateau in the response beginning at 10 ng/ml dose. There is no significant advantage to increasing the dose of TGF$\beta_1$ over 10 ng/mL as measured by this endpoint. Error bars represent the mean±SD for n=3.
Figure 9:
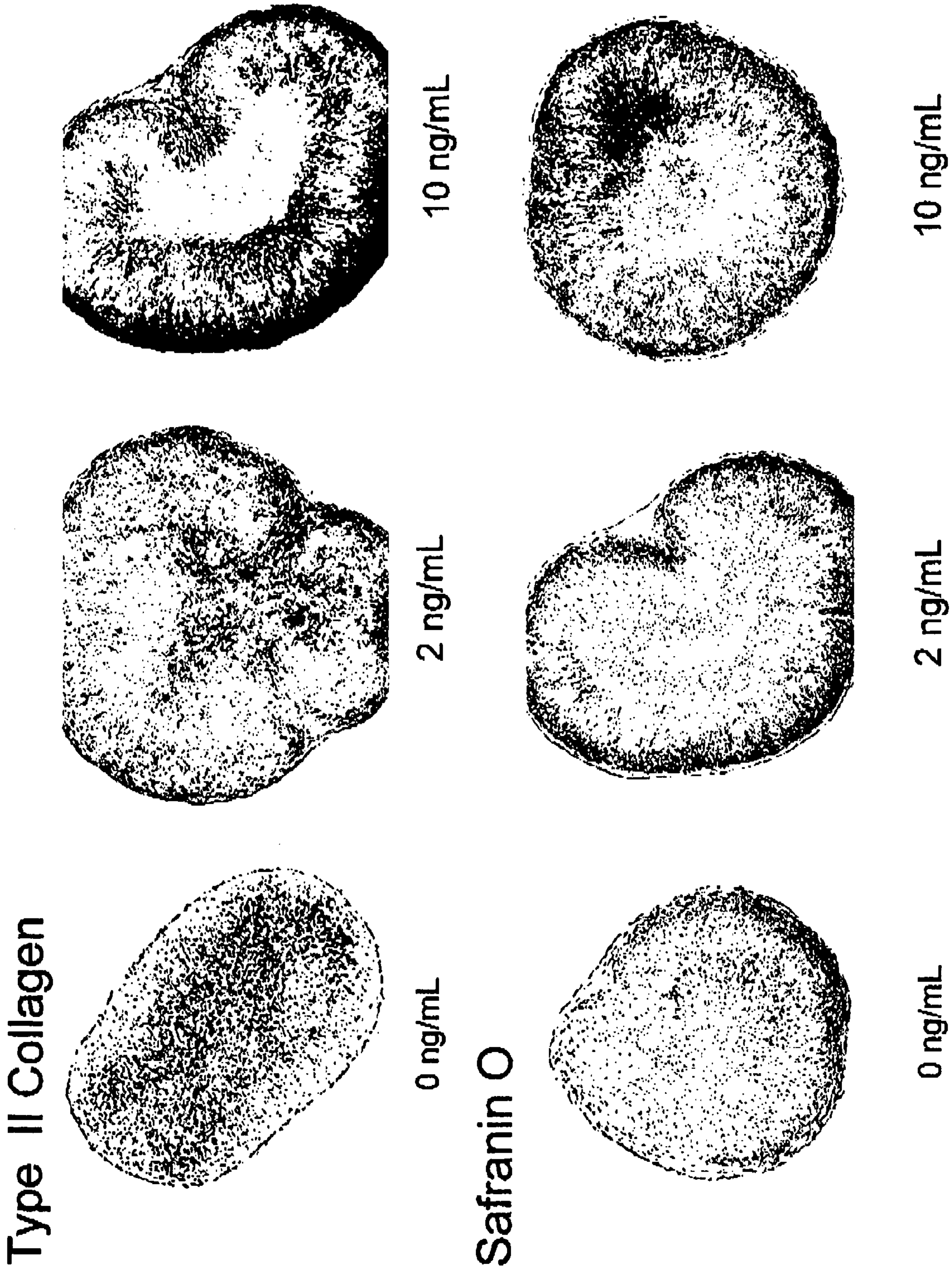
FIG. 9. Treatment of SF-B pellets with varied concentrations of TGF$\beta_1$. At Day 7, histological examination of pellets derived from SF-B cells showed an increase in Safranin-O staining for sulfated glycosaminoglycans as well as increased immunostaining with an antibody specific for collagen type II as the concentrations of the growth factor increased.

With the supplementation of $TGF\beta_1$, SF-B pellets yielded significantly higher aggrecan and collagen II mRNA expression at Day 7 (FIG. 7). With increasing concentrations of $TGF\beta_1$ from 0 to 10 ng/mL, an increasing concentration of GAG per pellet was observed. A plateau was reached at 10 ng/mL (FIG. 8). To maintain GAG concentrations at a similar level for culture periods longer than 14 days, the concentration of $TGF\beta_1$ needed to be increased to 20 ng/mL. Histological analysis indicated that a more extensive distribution of GAG and collagen type II was present in SF-B pellets exposed to a $TGF\beta_1$ concentration of 10 ng/ml (FIG. 9).

Isolated Type B Synoviocytes for Repair of Orthopedic Tissue

Human chondroprogenitor cells of synovial origin sustain their high proliferation potential and capacity to differentiate into chondrocytes in culture regardless of the donor's age. Type B synovial cells are effective in the repair of large and small joint and cartilage defects and providing stronger anchor support for tendon repairs. Supplementation of growth factors from the $TGF\beta$ superfamily induces proliferation and differentiation.

The data described herein indicates that negative isolation by Dynal magnetic beads is a reliable and quick method for isolating SF-B from a mixed population of synovial cells. Following the digestion of synovium, three groups of cells are present in primary culture: monocytes/macrophages, fibroblast-derived cells, and non-adherent cells. The non-adherent cells are easily removed by a PBS rinse and medium change. Because the Dynabeads M-450 CD14 are designed with a monoclonal antibody specific for a superficial antigen of monocytes/macrophages, they can be used to negatively isolate macrophages in the digested cell suspension, leaving the SF-B fibroblasts remaining in the final suspension. The effectiveness of this method was demonstrated by real-time RT-PCR data, which shows that the relative expression level of CD14 increased following the removal of the non-adherent cells and decreased after the isolation and purification of SF-B. The relative expression level of vimentin increased significantly in the final supernatant containing the SF-B, after the removal of both the non-adherent cells and the monocytes/macrophages.

$TGF\beta_1$ promotes differentiation of SF-B cells in a dose dependent manner. $TGF\beta_1$ enhances the chondrogenic properties of cultured synovial explant tissue. Cartilage was produced using the classic pellet culture system along with $TGF\beta_1$ treatment. At all time points, the molecular, biochemical, and histological data indicated that the SF-B pellets were superior to MSCP in producing cartilage differentiation. The dose studies of $TGF\beta_1$ in the SF-B pellet cultures suggests that 10 ng/mL of $TGF\beta_1$ is a preferred concentration for producing the greatest cell number and cartilage extracellular matrix at 7 days of culture.

The results demonstrated that systematically that type B fibroblasts (SF-B) isolated from synovium are the cells responsible for cartilage differentiation. Theses results indicate a primary role for SF-B, a chondroprogenitor cell, not only in the progressively positive response in cartilage formation but also in chondrocyte maturation, thus indicating that SF-B aids the production of chondrogenesis in vivo.

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims.

Other aspects, advantages, and modifications considered to be within the scope of the following claims.

What is claimed is:

1. A method for inducing repair of a joint tissue in a mammal comprising:

a) removing a sample of synovial membrane from a joint of said mammal;

b) isolating type B synoviocytes from said membrane to yield a suspension enriched in type B synoviocytes, wherein said isolating type B synoviocytes further comprises removing type A synoviocytes from the suspension; and c) introducing said suspension into an injured joint of said mammal, wherein said method does not comprise in vitro cell culture to expand the number of cells.

2. The method of claim 1, wherein said type A synoviocytes are removed by negative selection of cells expressing a macrophage- or monocyte-cell surface antigen.

3. The method of claim 1, wherein said type A synoviocytes are removed by separation with magnetic polymeric beads coated with a ligand that binds to a macrophage- or monocyte-specific antigen.

4. The method of claim 3, wherein said ligand is an antibody or antigen-binding fragment thereof and said antigen is CD 14.

5. The method of claim 1, wherein said type B synoviocytes are maintained ex vivo for less than 120 minutes.

6. The method of claim 1, wherein said type B synoviocytes are maintained ex vivo for less than 90 minutes.

7. The method of claim 1, wherein said type B synoviocytes are maintained ex vivo for less than 60 minutes.

8. The method of claim 1, wherein said suspension of enriched type B synoviocytes are contacted with a growth factor prior to introduction into said injured joint.

9. The method of claim 8, wherein said growth factor is selected from the group consisting of TGFβ1, FGF2, PDGFβ, IGF1, BMP-2, BMP-4, and BMP-7.

10. The method of claim 1, wherein said suspension of enriched type B synoviocytes are subjected to a physical or electromagnetic force prior to introduction into said injured joint.

11. The method of claim 1, wherein said method further comprises administering a growth factor into said joint.

12. The method of claim 1, wherein said mammal is a human.

* * * * *